(12) United States Patent
Carver

(10) Patent No.: US 8,883,747 B1
(45) Date of Patent: Nov. 11, 2014

(54) TOPICAL ANTIFUNGAL COMPOSITIONS AND METHODS OF USE THEREOF

(71) Applicant: Craig W. Carver, Ball Ground, GA (US)

(72) Inventor: Craig W. Carver, Ball Ground, GA (US)

( * ) Notice: Subject to any disclaimer, the term of this patent is extended or adjusted under 35 U.S.C. 154(b) by 0 days.

(21) Appl. No.: 14/050,094

(22) Filed: Oct. 9, 2013

(51) Int. Cl.
| | |
|---|---|
| A01N 43/04 | (2006.01) |
| A61K 31/70 | (2006.01) |
| A01N 43/50 | (2006.01) |
| A61K 31/415 | (2006.01) |
| C07H 17/08 | (2006.01) |
| C07D 233/56 | (2006.01) |
| C07D 233/58 | (2006.01) |
| A61K 31/7048 | (2006.01) |
| A61K 31/4174 | (2006.01) |
| A61K 31/4178 | (2006.01) |
| A61K 45/06 | (2006.01) |

(52) U.S. Cl.
CPC ......... *A61K 31/7048* (2013.01); *A61K 31/4174* (2013.01); *A61K 31/4178* (2013.01); *A61K 45/06* (2013.01)
USPC ............ 514/30; 514/396; 536/6.5; 548/346.1

(58) Field of Classification Search
USPC ................ 514/31.396, 30, 396; 536/6.5; 548/344.1, 346.1
See application file for complete search history.

(56) References Cited

U.S. PATENT DOCUMENTS

| | | | | |
|---|---|---|---|---|
| 4,267,169 | A | * | 5/1981 | Kamishita et al. ............ 514/396 |
| 4,454,118 | A | * | 6/1984 | Johnson ........................ 424/537 |
| 6,080,744 | A | * | 6/2000 | Ayon-Covarrubias ... 514/254.07 |
| 6,740,326 | B1 | | 5/2004 | Meyer et al. |
| 7,811,599 | B2 | | 10/2010 | Lukacs et al. |
| 2004/0018242 | A1 | * | 1/2004 | Cunningham et al. ........ 424/489 |
| 2005/0043251 | A1 | | 2/2005 | Lane |
| 2012/0128612 | A1 | | 5/2012 | Lenn et al. |
| 2013/0059019 | A1 | | 3/2013 | Leighton et al. |

FOREIGN PATENT DOCUMENTS

| | | | |
|---|---|---|---|
| CN | 101601750 A | * | 12/2009 |
| WO | 2011061155 | | 5/2011 |

OTHER PUBLICATIONS

Saleh et. al., Alexandria Journal of Pharmaceutical Sciences, 2011, publisher unknown, vol. 25, issue 2, pp. 103-106.*
Scheinfeld, N. et al, "A Primer of Skin Diseases Associated With Obesity", Expert Rev Dermatol. 2007;2(4):409-415.
"Antifungal Agents for Common Pediatric Infections," Pediatric Child Health, Nov.-Dec. 2000; 5(8), 477-482.
Ward, D. et al, "Characterization of Diaper Dermatitis in the United States", JAMA Pediatrics, vol. 154, No. 9, Sep. 2000.
Mistiaen, P. et al, "Prevention and treatment of intertrigo in large skin folds of adults: A systematic review", BioMed Central, BMC Nurs. 2010; 9: 12 Published online Jul. 13, 2010. Doi: 10.1186/1472-6955-9-12.
"Nystatin" Clinical Pharmacology, Copyright c 2013 Elsevier/Gold Standard (http://www.clinicalpharmacology.com/).
Gupta, A. et al, "Management of diaper dermatitis", International Journal of Dermatology, vol. 43, Issue 11, pp. 830-834, Nov. 2004.
Visscher, M., "Recent Advances in Diaper Dermatitis: Etiology and Treatment", Pediatr Health. 2009:3(1):81-98.

* cited by examiner

*Primary Examiner* — Sarah Pihonak
(74) *Attorney, Agent, or Firm* — Gardner Groff Greenwald & Villanueva, PC

(57) ABSTRACT

Described herein are compositions and methods that treat fungal infections of the skin, reduce the severity and duration of symptoms of fungal infections of the skin, and prevent recurrence of fungal infections. The topical compositions described herein are creamy pastes composed of an admixture of an imidazole antifungal and nystatin. The topical compositions can also include optional fillers. The compositions and methods described herein minimize fungal resistance and maximize the number of targeted fungal strains. Additionally, the compounds and methods do not suppress the body's immune system either locally or systemically, thus allowing for a faster restoration of normal skin flora. The compositions and methods described herein are particularly suitable for use in infants and children as well as in immunocompromised individuals, diabetics, and the obese.

8 Claims, No Drawings

TOPICAL ANTIFUNGAL COMPOSITIONS AND METHODS OF USE THEREOF

BACKGROUND

The superficial layers of the skins and mucous membranes of humans and other animals play host to a variety of microorganisms, including numerous species of fungi and bacteria. Balance between skin flora and the host organisms is normally maintained at a steady level, but uncontrolled fungal growth occurs regularly in the obese, in diabetics, and in immunocompromised individuals such as cancer patients undergoing chemotherapy, HIV positive persons, and transplant recipients taking anti-rejection drugs, among others.

*Candida albicans* occurs naturally on the body, particularly in warm, moist areas. Intertrigo is an overgrowth of *Candida* yeast in areas such as the groin, armpits, between the buttocks, under heavy breasts, the inner thighs, the perianal area, the genital area, between the toes, the crease of the neck, between abdominal fat folds, and other body surfaces. Intertrigo also presents as diaper rash. Overgrowth of yeasts such as *Candida* is particularly problematic in institutional settings; prevalence ranges from 6% of hospital patients to 17% of those residing in nursing homes. Up to 20% of homebound patients also experience topical yeast imbalances. Any persons experiencing restricted mobility may be at increased risk for intertrigo. Other contributing factors include incontinence, heat, humid weather, tight clothing, lack of air circulation, friction between skin folds, excessive sweating, poor hygiene, malnutrition, inflammatory skin conditions such as psoriasis, and the use of topical steroids.

Candidal diaper dermatitis (diaper rash) is a common yeast overgrowth infection caused by *C. albicans* that frequently presents in the perianal area and between the buttocks of infants and toddlers. Visits to outpatient pediatric offices for diaper rash total one million per year in the United States. The skin of infants is thinner than that of adults and produces fewer secretions. Thus, infant skin is more susceptible to irritation and infection. Measures such as frequent diaper changes, avoidance of moisture-impervious diaper covers, and leaving children for long periods of time without diapers can help prevent diaper rash. However, topical antifungal therapy is still necessary for the resolution of candidal diaper rash.

Symptoms of *Candida* imbalance include redness, irritation, intense itching, burning, pain, and odor. Physicians often prescribe combination steroid/antifungal creams such as Mycolog (nystatin/triamcinolone), Lotrisone (clotrimazole/betamethasone), or Vytone (iodoquinol/hydrocortisone), to intertrigo patients. While these rapidly relieve symptoms, fungal resurgence after corticosteroid treatment is common. These recurrences of symptoms often exceed the initial presentation. Although traimcinolone, betamethasone, and hydrocortisone provide immediate relief of symptoms, they also suppress the body's own immune response in the inflamed and/or macerated areas. Thus, a need exists for a non-steroidal treatment for *Candida* overgrowth and intertrigo.

SUMMARY

Described herein are compositions and methods that treat fungal infections of the skin, reduce the severity and duration of symptoms of fungal infections of the skin, and prevent recurrence of fungal infections. The topical compositions described herein are creamy pastes composed of an admixture of an imidazole antifungal and nystatin. The topical compositions can also include optional fillers. The compositions and methods described herein minimize fungal resistance and maximize the number of targeted fungal strains. Additionally, the compounds and methods do not suppress the body's immune system either locally or systemically, thus allowing for a faster restoration of normal skin flora. The compositions and methods described herein are particularly suitable for use in infants and children as well as in immunocompromised individuals, diabetics, and the obese.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "an imidazole antifungal" includes mixtures of two or more such antifungals, and the like.

"Optional" or "optionally" means that the subsequently described event or circumstance can or cannot occur, and that the description includes instances where the event or circumstance occurs and instances where it does not. For example, the phrase "optionally includes an excipient inert powder" means that the inert powder can or cannot be included in the composition and that the description includes compositions where the powder is included and compositions where it is not included.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

By "subject" is meant an individual. The subject can be a mammal such as a primate or a human. The term "subject" can include domesticated animals including, but not limited to, cats, dogs, etc., livestock (e.g., cattle, horses, pigs, sheep, goats, etc.), and laboratory animals (e.g., mouse, rabbit, rat, guinea pig, etc.).

By "contacting" is meant an instance of exposure by close physical contact of at least one substance to another substance. For example, contacting can include contacting a body surface, such as the skin of a subject, with a topical composition described herein.

"Treatment" or "treating" means to administer a composition to a subject or a system with an undesired condition (e.g., fungal infection) to reduce the symptoms of the undesired condition when compared to the same subject that is not administered the composition. The compositions described herein can reduce or arrest (i.e., stop) fungal growth in a subject. The topical compositions described herein can be applied directly to the infected area on the subject and/or near the then infected area.

In other aspects, the compositions described herein can prevent fungal growth in a subject. Here, the topical compositions described herein can be applied to an area of the subject that is prone to fungal infection.

By "effective amount" is meant a therapeutic amount needed to achieve the desired result or results.

"Topical" refers to a composition that is applied to the surface of a subject's body. Topical compositions may be applied, for example, to the skin, mucous membranes, hair, nails, or any other exposed surface of the body.

A "fungal infection" is the invasion of the body by pathogenic fungi. This invasion can produce tissue injury and/or discomfort for the infected individual. Fungal infections can be opportunistic (e.g., resulting from overgrowth of skin microbiota during conditions of immune suppression) or can be acquired from the environment (e.g., nosocomial infections). An "antifungal" compound or composition is administered to subjects having fungal infections to kill as well as reduce or prevent the growth of fungi.

"Burow's solution" is an aqueous solution of aluminum acetate used in pharmacological applications, which may range in concentration from 5% to 13%, depending on the desired use. Burow's solution is commonly employed for control of symptoms associated with inflammatory skin conditions and also is known to have antibacterial properties. It is traditionally applied in a cold compress but can optionally be used as a cleanser or astringent.

An "excipient" is a pharmacologically inactive substance included in a pharmaceutical composition. Excipients are used for a variety of purposes including binders and fillers, coatings, colors and flavors, preservatives, sweeteners, and the like, and are frequently employed to aid in the distribution and/or dispensing of pharmaceutical preparations. An "inert" excipient is an excipient that will not react, biologically or chemically, with the other components of the composition of which it is a part.

"Powder" is composed of fine particles. Dry substances may be reduced to powders by techniques such as, for example, grinding, pounding, or triturating.

An "azole" is a five-membered nitrogen heterocyclic ring containing at least one other non-carbon atom. An "imidazole" is an azole containing two nitrogen atoms separated by one carbon atom. An "antifungal imidazole" is a compound that possesses antifungal properties and contains at least one imidazole ring substituent. The imidazole ring can optionally be further substituted. Imidazole antifungals can include, but are not limited to, clotrimazole, miconazole, ketoconazole, econazole, oxiconazole, and combinations thereof.

I. Compositions and Preparation Thereof

Described herein are topical compositions that reduce, arrest, or prevent fungal growth in a subject. In one aspect, the compositions include imidazole antifungal compounds and nystatin powder. In another aspect, the compositions include imidazole antifungal compounds, nystatin powder, and excipient inert powders. In a further aspect, the imidazole antifungal compounds are selected from clotrimazole, ketoconazole, miconazole, oxiconazole, econazole, or combinations thereof. In a still further aspect, the excipient inert powders are selected from corn starch, talc, or combinations thereof. In one aspect, the compositions are topical compositions. In another aspect, the compositions are formulated in creamy paste dosage forms.

Not wishing to be bound by theory, imidazole antifungals mechanistically have been shown or proposed to inhibit biosynthesis of the fungal sterol ergosterol, to interact with membrane phospholipids, to inhibit endogenous respiration, and to inhibit transformation of yeasts to mycelial forms. Meanwhile, antifungal properties of polyenes such as nystatin are linked to binding ergosterol. Thus, the beneficial effects of combining imidazole antifungals and polyenes into a single treatment composition have never before been realized; these two classes of antifungals are not typically combined since it is thought that the presence of one (imidazoles) reduces the number of binding sites available for the other (nystatin).

The present compositions are based on the surprising discovery that combinations of imidazole-containing creams and/or lotions with nystatin powder demonstrate superior efficacy with respect to symptom control, reduction in severity of fungal infections, and therapeutic resolution of symptoms. Further, it has been discovered that a creamy paste dosage form of the above combination is more effective than either a straight powder formulation or a powderless cream.

The mixtures and combinations described herein are, therefore, superior alternatives to conventional treatments consisting of singular antifungals and/or antifungal/steroid combinations. Additionally, a combination of two active ingredients such as in the compositions described herein will be able to effectively eliminate or reduce the growth of strains resistant to one, but not both, active ingredients. Thus, the mixtures and compositions described herein possess significant advantages over conventional treatments when dealing with complicated cases and/or simultaneous infections by multiple strains of fungi.

Each component used to prepare the topical formulations described herein is discussed in detail below.

Imidazole Antifungal

In one aspect, the imidazole antifungal is used with a pharmaceutically acceptable topical carrier. Various creams, lotions, and topical solutions of the imidazole antifungal can be used herein. The lotion, cream or solution can be any pharmaceutically acceptable excipient that can be topically applied to a subject.

In one aspect, the imidazole antifungal is 0.5%, 1%, 1.5%, 2%, 2.5%, 3%, 3.5%, 4%, 4.5%, or 5% by weight of the imidazole composition. Examples of imidazole antifungal compositions useful herein include, but are not limited to, 1% clotrimazole cream, 1% clotrimazole lotion, 1% clotrimazole topical solution, 2% ketoconazole cream, 2% miconazole nitrate cream, 1% oxiconazole nitrate cream, 1% oxiconazole nitrate lotion, 1% econazole nitrate cream, and combinations thereof. In one aspect, the active and inert ingredients of the compositions meet United States Pharmacopeia (USP) standards for quality, purity, and dosage.

Nystatin

Nystatin is a polyene antifungal medication. In one aspect, nystatin can be used herein as a powder or cream. In one aspect, the nystatin powder or cream has an activity of 10,000 units/gram to 500,000 units/gram; 50,000 units/gram to 250,000 units/gram; 75,000 units/gram to 150,000 units/gram, or 100,000 units/gram. In one aspect, nystatin powder is formulated with talc or another pharmaceutically acceptable excipient.

Preparation of Topical Compositions

The topical compositions described herein are formulated as creamy pastes. A "creamy paste" is a cream, lotion, or solution that has been thickened due to the addition of one or more solid ingredients. For example, the creamy paste can be prepared by admixing granular particles in a cream or lotion so that the particles are evenly distributed and suspended in the cream or lotion. The source of the granular particles can vary. In one aspect, the nystatin is a powder, which is the source of the granular materials. The amount of the granular particles can also vary depending upon the moisture levels in the environment. For example, in hot, humid conditions, the higher amounts of granular particles can be included in the composition.

In another aspect, when the imidazole antifungal and nystatin are both a cream or lotion, one or more inert granular powders can be added to produce the creamy pastes described herein. In one aspect, the excipient inert powder reduces the active ingredient concentrations of imidazole antifungal compound and/or nystatin. Reduced concentrations of active ingredients are desirable for the treatment of certain patients such as, for example, children with diaper rash or other sensitive individuals. In this aspect, the concentrations of active ingredients are reduced to safe, but still efficacious, levels for these subjects.

Additionally, the excipient inert powder can impart sweat and/or moisture absorption capabilities to the compositions described herein. In one aspect, this absorption capability is believed to be beneficial because it reduces the suitability of the affected areas for further fungal growth. In still another aspect, the excipient inert powder acts as a skin lubricant to reduce the skin friction, chafing, and discomfort that are common to intertrigo, candidal diaper dermatitis, and other fungal infections of the skin.

Examples of excipient inert powders useful herein include, but are not limited to, corn starch, talc, or a combination thereof.

In one aspect, the creamy pastes described herein are composed of 10% to 80% granular particles, where the source of the granular particles is nystatin powder, the inert powder, or both the nystatin powder and the inert powder. In another aspect, the creamy paste is composed of 10%, 15%, 20%, 25%, 30%, 35%, 40%, 45%, 50%, 55%, 60%, 65%, 70%, 75%, or 80% by granular particles (nystatin powder and/or inert powder), where any value can form a lower and upper end-point of arrange.

In one aspect, the topical composition is a creamy paste composed of 20% to 80% by weight imidazole (1% or 2% cream), and 20% to 80% by weight nystatin powder (100,000 units/gram). In another aspect, the topical composition is composed of 30% to 70%, 40% to 70%, 50% to 70%, or 60% by weight imidazole (1% or 2% cream), and 20% to 70%, 30% to 60%, 30% to 50%, or 40% by weight nystatin powder (100,000 units/gram).

In another aspect, the topical composition is a creamy paste composed of 1% clotrimazole USP cream and nystatin powder having an activity of 100,000 units/gm, wherein the weight ratio of clotrimazole to nystatin powder is from 1:1 to 5:1; 1:1 to 4:1; 1:1 to 3:1; 1:1 to 2: for about 3:2.

In one aspect, the topical composition is one of the following:
1. At least 50% of an imidazole cream, lotion, or solution, and at least 25% of Nystatin Topical Powder USP (100,00 units/gm).
2. Clotrimazole Cream USP (1%) and Nystatin Topical Powder USP (100,000 units/gm) in a 2:1 weight ratio.
3. Clotrimazole Cream USP (1%) and Nystatin Topical Powder USP (100,000 units/gm) in a 3:2 weight ratio.
4. Clotrimazole Lotion USP (1%) and Nystatin Powder USP (100,000 units/gm) in a 3:2 weight ratio.
5. Clotrimazole Lotion USP (1%) and Nystatin Topical Powder USP (100,000 units/gm) in a 2:1 weight ratio.
6. Clotrimazole Topical Solution USP (1%) and Nystatin Topical Powder USP (100,000 units/gm) in a 2:1 weight ratio.
7. Clotrimazole Topical Solution USP (1%) and Nystatin Topical Powder USP (100,000 units/gm) in a 3:2 weight ratio.
8. Ketoconazole Cream USP (2%) and Nystatin Topical Powder USP (100,000 units/gm) in a 2:1 weight ratio.
9. Ketoconazole Cream USP (2%) and Nystatin Topical Powder USP (100,000 units/gm) in a 3:2 weight ratio.
10. Miconazole Nitrate Cream USP (2%) and Nystatin Topical Powder (100,000 units/gm) in a 2:1 to 3:2 weight ratio.
11. Oxiconazole Nitrate Cream or lotion (1%) and Nystatin Topical Powder USP (100,000 units/gm) in a 2:1 to 3:2 weight ratio.
12. Econazole Nitrate Cream (1%) and Nystatin Topical Powder USP (100,000 units/gm) in a 2:1 to 3:2 weight ratio.

In one aspect, the composition includes less than or equal to 50% by weight of an imidazole cream, lotion, or solution (1% or 2%), less than or equal to 40% by weight Nystatin Cream or powder USP (100,000 units/gm), and less than or equal to 40% inert powder, wherein the sum of the components is 100%.

In one aspect, the topical composition is one of the following:
1. Clotrimazole Cream USP (1%), Nystatin Cream USP (100,000 units/gm), and Corn Starch USP in a 40%/30%/30% by weight mixture.
2. Clotrimazole Cream USP (1%), Nystatin Cream USP, (100,000 units/gm), and Corn Starch USP in a 35%/30%/35% weight mixture.
3. Clotrimazole Cream USP (1%), Nystatin Cream USP, (100,000 units/gm), and Corn Starch USP in a 50%/25%/25% weight mixture.
4. Clotrimazole Lotion USP (1%), Nystatin Cream USP (100,000 units/gm), and Corn Starch USP in a 40%/25%/35% weight mixture.
5. Clotrimazole Lotion USP (1%), Nystatin Cream USP (100,000 units/gm), and Corn Starch USP in a 50%/20%/30% weight mixture.
6. Clotrimazole Cream USP (1%), Nystatin Cream USP (100,000 units/gm), and Talc USP in a 40%/30%/30% weight mixture.
7. Clotrimazole Cream USP (1%), Nystatin Cream USP (100,000 units/gm), and Talc USP in a 35%/30%/35% weight mixture.
8. Clotrimazole Cream USP (1%), Nystatin Cream USP (100,000 units/gm), and Talc USP in a 50%/25%/25% weight mixture.
9. Clotrimazole Lotion USP (1%), Nystatin Cream USP (100,000 units/gm), and Talc USP in a 40%/25%/35% weight mixture.
10. Clotrimazole Lotion USP (1%), Nystatin Cream USP (100,000 units/gm), and Talc USP in a 50%/20%/30% weight mixture.
11. Miconazole Nitrate Cream USP (2%), Nystatin Cream USP (100,000 units/gm), and Corn Starch USP in a 40%/30%/30% weight mixture.
12. Miconazole Nitrate Cream USP (2%), Nystatin Cream USP (100,000 units/gm), and Corn Starch USP in a 35%/30%/35% weight mixture.

13. Miconazole Nitrate Cream USP (2%), Nystatin Cream USP (100,000 units/gm), and Corn Starch USP in a 50%/25%/25% weight mixture.
14. Miconazole Nitrate Cream USP (2%), Nystatin Cream USP (100,000 units/gm), and Talc USP in a 40%/30%/30% weight mixture.
15. Miconazole Nitrate Cream USP (2%), Nystatin Cream USP (100,000 units/gm), and Talc USP in a 35%/30%/35% weight mixture.
16. Miconazole Nitrate Cream USP (2%), Nystatin Cream USP (100,000 units/gm), and Talc USP in a 50%/25%/25% weight mixture.
17. Oxiconazole Nitrate Cream (1%), Nystatin Cream USP (100,000 units/gm), and Corn Starch USP in a 40%/30%/30% weight mixture.
18. Oxiconazole Nitrate Cream (1%), Nystatin Cream USP (100,000 units/gm), and Corn Starch USP in a 35%/30%/35% weight mixture.
19. Oxiconazole Nitrate Cream (1%), Nystatin Cream USP (100,000 units/gm), and Corn Starch USP in a 50%/25%/25% weight mixture.
20. Oxiconazole Nitrate Lotion (1%), Nystatin Cream USP (100,000 units/gm), and Corn Starch USP in a 40%/25%/35% weight mixture.
21. Oxiconazole Nitrate Lotion (1%), Nystatin Cream USP (100,000 units/gm), and Corn Starch USP in a 50%/20%/30% weight mixture.
22. Oxiconazole Nitrate Cream (1%), Nystatin Cream USP (100,000 units/gm), and Talc USP in a 40%/30%/30% weight mixture.
23. Oxiconazole Nitrate Cream (1%), Nystatin Cream USP (100,000 units/gm) and Talc USP in a 35%/30%/35% weight mixture.
24. Oxiconazole Nitrate Cream (1%), Nystatin Cream USP (100,000 units/gm), and Talc USP in a 50%/25%/25% weight mixture.
25. Oxiconazole Nitrate Lotion (1%), Nystatin Cream USP (100,000 units/gm), and Talc USP in a 40%/25%/35% weight mixture.
26. Oxiconazole Nitrate Lotion (1%), Nystatin Cream USP, 100,000 units/gm, and Talc USP in a 50%20%/30% weight mixture.

It will be appreciated that the actual preferred amounts of active imidazole antifungal and nystatin in a specified case will vary according to the specific compound being utilized, the particular compositions formulated, the mode of application, and the particular sites and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing—1999).

The pharmaceutical compositions can also include other drugs and biologically-active agents. The biologically-active agent is capable of providing a local or systemic biological, physiological or therapeutic effect in the biological system. For example, the agent can act to control infection or inflammation, enhance cell growth and tissue regeneration, or act as an analgesic, among other functions. Thus, combination therapies are contemplated where the compositions described herein can reduce the severity of or eliminate fungal infection in combination with other therapeutic benefits.

II. Methods of Use

The compounds and pharmaceutical compositions described herein can be used in a variety of applications related to the treatment of fungal infections. A method for treating a fungal infection includes contacting an area showing symptoms of a fungal infection with the compositions defined above.

In one aspect, the fungi causing the infection are yeasts such as, for example, *Candida albicans* or other *Candida* spp. including *C. glabrata, C. rugosa, C. parapsilosis, C. tropicalis,* or *C. dubliniensis* In another aspect, the fungi are dermatophytes such as, for example, *Trichophyton* spp. and *Microsporum* spp. In a further aspect, the dermatophytes are *Epidermophyton floccosum, T. rubrum, T. interdigitale, T. tonsurans, T. violaceum, T. concentricum, T. schoenleinii, T. soudanense, T. mentagrophytes, T. equinum, T. erinacei, T. verrucosum, M. audouinii, M. ferrugineum, M. canis, M. gypseum, M. nanum,* and/or *M. cookei.*

In another aspect, the fungal infection causes a fungal disease such as, for example, tinea cruris, tinea corporis, tinea versicolor, candidiasis, tinea pedis, intertrigo, seborrhoeic dermatitis, diaper rash, tinea capitis, tinea barbae, thrush, diaper dermatitis (children and adults) or a combination thereof. In a still further aspect, the fungal disease causes symptoms such as, for example, itching, a burning sensation, flaking skin, peeling skin, rash, redness, cracking skin, scaly skin, blisters, macerated skin, odor, or a combination thereof.

In one aspect, the compositions described herein are useful in treating or preventing intertrigo. Intertrigo is an inflammation or rash caused by overgrowth of yeast species such as, for example, *Candida albicans*. Intertrigo afflicts areas of the body that have skin touching skin such as the groin, armpits, between the buttocks, under heavy breasts, in the inner thighs, beneath penile foreskin, the perianal area, genital area, between the toes, in the crease of the neck, and abdominal fat folds provide the perfect environment for *Candida albicans* imbalance and symptom presentation. The body heat and moisture present in these intertriginous areas provide a prime milieu for the proliferation of yeasts such as *Candida*, leading to irritation, redness, intense itching, burning, pain and odor. Maceration and/or characteristic satellite reddened plaques/lesions often present under the breast, in the abdominal folds, and in the inguinal area. Intertrigo frequently presents as candidal diaper rash as well.

Factors that frequently cause or contribute to intertrigo include immune deficiencies, obesity, diabetes, incontinence, heat, humid weather, tight or abrasive clothing or underclothing, lack of air circulation, friction between skin folds, excessive sweating and moisture, poor hygiene, malnutrition, inadequate bra support, inflammatory skin conditions like psoriasis in skin folds, and the use of topical steroids. Infants and toddlers, with their chubbiness, shorter necks, and bended posture, are also at increased risk for intertrigo.

Intertrigo is also particularly common among immunocompromised patients. "Immunocompromised patients" are individuals with weakened immune systems resulting from, for example, HIV or AIDS, chemotherapy and/or radiation such as for cancer treatment, long-term corticosteroid or glucocorticoid therapy, anti-rejection drugs taken by transplant recipients, cancers of the bone marrow or the blood, splenectomy, or congenital deficiencies.

In another aspect, the compositions described herein are useful in treating or preventing candidal diaper rash. Candidal diaper dermatitis (i.e., diaper rash) is a common yeast overgrowth infection caused by *Candida albicans* that frequently presents in the perianal area and between the buttocks of infants and toddlers. Visits to outpatient pediatric offices for diaper dermatitis total 1 million per year. Infant skin is thinner than that of adults, produces fewer secretions, and is more susceptible to irritation and infection. Measures to decrease maceration of the skin in these areas include frequent diaper changes, avoiding impervious diaper covers, and long periods without diapers. Still, topical antifungal therapy is necessary for resolution of candidal diaper rash.

The compositions described herein can be used to treat fungal infections and diseases and also to reduce the severity of or eliminate symptoms caused by fungal infections and diseases. In one aspect, a method for treating a fungal disease in a subject is provided. In this aspect, a subject is contacted with an effective amount of one or more of the antifungal compositions described herein. In a further aspect, the subject is a mammal. In a still further aspect, the mammal is a human or other primate, a cat, a dog, cattle, a horse, a pig, a sheep, a goat, a mouse, a rabbit, a rat, a guinea pig, or any other domesticated, captive, or livestock mammal.

In a further aspect, the method involves contacting the affected area(s) of a subject with the compositions described herein. This contact may occur one, two, three, or four times daily. In one aspect, the topical compositions described herein can be applied to an area that is susceptible to fungal infection. In this aspect, the topical compositions described herein can prevent infection by the fungus.

In another aspect, the method involves initiating treatment at the onset of symptoms associated with fungal infection or disease. In another aspect, the method involves initiating treatment at any time after the onset of symptoms associated with fungal infection or disease. In one aspect, treatment is stopped upon resolution of the symptoms associated with fungal infection or disease. In another aspect, treatment is continued after the resolution of the symptoms. In this aspect, continued treatment is believed to help prevent the recurrence of symptoms and/or the resurgence of resistant fungal strains. In still another aspect, treatment may be continued for 1, 2, 3, 4, 5, 6, or up to 7 days after the resolution of symptoms. In yet another aspect, the compositions may be applied sparingly or liberally to the affected area. In some aspects, the affected area is washed with water or a mild soap prior to application of the compositions described herein.

In a still further aspect, the methods and compositions described herein specifically exclude topical and/or systemic treatment with glucocorticoids. Thus, the compositions and mixtures disclosed herein can aid in the restoration of natural flora balance and skin fold integrity without the use of glucocorticoids.

In the alternative, a glucocorticoid compound and the compositions described herein can be simultaneously administered. In another aspect, the compositions described herein can include other active antifungal ingredients or other ingredients that provide immediate relief from symptoms associated with fungal infection and disease.

In one aspect, the area to be treated is first pretreated prior to application of the topical compositions described herein. For example, the area of the subject can be first contacted with Burow's solution, either topically or included as part of a cold compress, prior to application of the compositions described herein. In this aspect, Burow's solution cleanses the affected area and/or allows the subject immediate relief from symptoms such as itching, burning, and the like. Prior to application of the topical application, the area to be treated should be dried as thoroughly as possible, as moisture can promote fungal growth on the skin.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Trial 1

An obese female with severe chemotherapy-related inguinal intertrigo was treated and observed. Initially, one-dimensional therapy with clotrimazole cream 1% applied 3 times a day neutralized progression within 4 days, but she remained uncomfortably symptomatic and tissues remained red and still macerated in part due to continued sweating in the infected area.

Nystatin-Triamcinolone cream was instituted on day 5 due to unrelenting itching, burning, and inflammation in the groin. Symptomatic relief followed within 2 days and applications of the antifungal-steroid cream combination continued for 10 days with substantial symptomatic and apparent therapeutic resolution. However, recurrence and escalation resumed a week later following this apparent resolution.

Aware of the possible risks associated with prolonged steroid use, the following antifungal agents were singularly employed: ketoconazole cream 2% was applied 2 to 3 times a day with significant yet marginal lasting efficacy, and discontinuation after 8 days was followed with miconazole cream 2% applied 2 to 3 times a day for more than 7 days. Antimicrobial therapy was discontinued and Baby Powder (talc) was applied twice a day, which appeared to enable integumentary improvement in a dry, chemical-free environment; redness, inflammation, and maceration abated significantly.

Nystatin powder was then "tested" near onset of the next recurrence; bathing or cleansing and drying of affected and surrounding tissues preceded application two or three times a day. Substantial improvement ensued initially and appeared to provide a more sustainable healing "environment", though intertrigo presented repeatedly from time to time.

Creamy paste dosage formulations of the present invention were subsequently evaluated. Although several creamy paste dosage formulations described herein were efficacious, the female subject responded best to a creamy pasty clotrimazole cream/nystatin powder formulation (a mixture of 20 grams of nystatin powder spatulated into 30 grams of clotrimazole cream). Higher degrees of pastiness were employed in increasingly elevated moisture situations with correspondingly favorable results. Resolution lasting months was achieved in the inguinal and upper thigh regions as well as occasional flare-ups under heavy breasts. Repeated yet far less frequent challenges over several years yielded consistent, superior and reliable results. The cycle of recalcitrance and frequent resurgence has remained resolved in this subject for the past 3 years.

Trial 2

A second obese, elderly female subject experienced similar favorable and lasting results using a creamy paste dosage formulations (20 grams of nystatin powder spatulated into 30 grams of clotrimazole cream) described herein following decades of frequent intertrigo treatment with conventional single-entity antifungal creams or powders and antifungal/steroid combinations. This subject also continues to rely on swift, predictable, and lasting resolution from occasional flare-ups.

Trial 3

A third male subject who experienced occasional intertrigo over several years was evaluated. Nystatin-triamcinolone cream was initially prescribed and applied twice daily on the infected areas. Although significant relief from intense itching and burning was achieved within 3 days followed by a 90% reduction in inflammatory presentation within 2 weeks, reoccurrence ensued a week later with heat and exercise-induced sweating as aggravating factors. Once again, nystatin-triamcinolone cream reduced symptoms within a few days, and nystatin cream was applied twice a day for 3 more weeks but total resolution would not occur.

Other antimicrobial creams including miconazole nitrate, clotrimazole, and ketoconazole were intermittently applied in successive flare-up situations over the next 4 months; however, lasting resolution appeared unachievable as this cycle of recalcitrant yeast overgrowth refused to respond and abate with conventional pharmaceuticals.

Next, several topical herb formulas containing various blends of calendula, tea tree oil, chamomile, echinacea, ginger, coconut oil, rosemary, organic jatoba, olive oil, thyme, vitamin E, lavender, and other pure essential oils were evaluated. Mixtures of these components were also evaluated in order to maximize efficacy of the formulations. On several occasions, oral coconut oil capsules and iodine tablets were employed without lasting impact or predictable efficacy. Topical lavender and tea tree oil formulations held the most utility but proved far too caustic when applied to macerated intertriginous regions. Most others simply lacked therapeutic benefit. Ultimately, none proved worthy of mention or recommendation from a pharmacist recognized as one who only endorses superior products in any category.

Finally, comprehensive intertrigo management beginning with application of a mixture of 20 grams of nystatin powder spatulated into 30 grams of clotrimazole cream interrupted the prolonged cycle of partial remission followed by recurrence, escalation, and recalcitrance. Varying degrees of pastiness were employed depending on degree of maceration, heat, and moisture presence. Affected and surrounding areas were cleansed and dried thoroughly prior to liberal application up to 4 times a day. Twice daily application proved sufficient after 4 days, and once daily maintenance with a creamier mixture after 10 days carried therapy to term on day 15. Ancillary measures employed at various stages of treatment included occasional and soothing burows solution astringent compresses and frequent underwear changes.

In the 5 years since, occasional flare-ups of inguinal and perineal intertrigo have occurred from time to time allowing opportunities for further validation of the utility of the formulation described above. Incredibly, microbial balance and skin fold healing is often restored within 3 days when treatment is initiated in a timely fashion. Though most complicated clinical presentations require 10 to 14 days, total microbial eradication and overkill is unnecessary when follow up measures to control heat and moisture are employed following symptom resolution and integumentary normalcy restoration.

For the sake of comparison, the subject was adminstered a 1:1 mixture of clotrimazole cream and nystatin cream to treat inguinal intertrigo that had spread to the scrotum. However, this formulation provided limited results when compared to the administration of the 3:2 clotrimazole cream/nystatin powder creamy paste, which was applied within 4 days with accelerated results consistent with above.

In summary, the formulations described herein are superior alternatives to current and standard singular antifungals and antifungal/steroid combinations in the treatment of intertrigo in complicated patient situations as well as prompt flare-up resolution of Candidal diaper dermatitis, which permits the resumption of barrier creams/ordinary protectants applied prophylactically.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A topical paste comprising
   (a) 1% clotrimazole cream and
   (b) nystatin powder comprising an inert powder having an activity of 100,000 units/gm,
   wherein the weight ratio of clotrimazole cream to nystatin powder is from 1:1 to 5:1 to form a paste comprising granular particles evenly distributed in the topical paste, and wherein the clotrimazole cream and nystatin powder are the only bioactive agents in the topical paste.

2. The paste of claim 1, wherein the excipient inert powder comprises corn starch, talc, or a combination thereof.

3. The paste of claim 1, wherein the weight ratio of clotrimazole to nystatin powder is from 1:1 to 2:1.

4. The paste of claim 1, wherein the weight ratio of clotrimazole to nystatin powder is 3:2.

5. A method for treating or preventing a fungal disease in a subject, the method comprising applying the paste of claim 1 to the subject, wherein the fungal disease is tinea cruris, tinea corporis, tinea versicolor, candidiasis, tinea pedis, intertrigo, seborrhoeic dermatitis, diaper rash, tinea capitis, tinea barbae, thrush, diaper dermatitis, or any combination thereof.

6. The method of claim 5, wherein the fungal disease is intertrigo.

7. The method of claim 5, wherein the fungal disease is diaper rash.

8. A method for treating a symptom of a fungal disease in a subject, the method comprising applying the paste of claim 1 to the subject, wherein the symptom is itching, a burning sensation, flaking skin, peeling skin, rash, redness, cracking skin, scaly skin, blisters, macerated skin, odor, or any combination thereof.

* * * * *